(12) United States Patent
Shin et al.

(10) Patent No.: US 8,900,144 B2
(45) Date of Patent: Dec. 2, 2014

(54) DIAGNOSIS APPARATUS AND METHOD OF OPERATING THE SAME

(75) Inventors: Dong-kuk Shin, Gangwon-do (KR); Jong-sik Kim, Gangwon-do (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 53 days.

(21) Appl. No.: 13/550,335

(22) Filed: Jul. 16, 2012

(65) Prior Publication Data
US 2013/0137983 A1 May 30, 2013

(30) Foreign Application Priority Data

Nov. 29, 2011 (KR) ........................ 10-2011-0126275

(51) Int. Cl.
*A61B 8/00* (2006.01)

(52) U.S. Cl.
USPC .......................................... 600/437; 382/128

(58) Field of Classification Search
USPC ........................... 600/437–469; 382/128–132
See application file for complete search history.

(56) References Cited

U.S. PATENT DOCUMENTS

| | | | |
|---|---|---|---|
| 5,127,409 A | 7/1992 | Daigle | |
| 6,558,324 B1 * | 5/2003 | Von Behren et al. | 600/440 |
| 6,589,176 B2 * | 7/2003 | Jago et al. | 600/443 |
| 8,532,430 B2 * | 9/2013 | Hazard | 382/275 |
| 8,539,838 B2 * | 9/2013 | Yoo et al. | 73/632 |
| 2003/0105401 A1 * | 6/2003 | Jago et al. | 600/443 |
| 2005/0085729 A1 * | 4/2005 | Abe | 600/450 |
| 2009/0292205 A1 * | 11/2009 | Osaka | 600/443 |
| 2010/0249595 A1 | 9/2010 | Xu et al. | |
| 2011/0015524 A1 * | 1/2011 | Suzuki et al. | 600/443 |
| 2011/0077518 A1 | 3/2011 | Miyachi | |
| 2011/0079083 A1 * | 4/2011 | Yoo et al. | 73/632 |
| 2011/0237945 A1 * | 9/2011 | Foroughi et al. | 600/438 |
| 2012/0108965 A1 | 5/2012 | Lazebnik | |

FOREIGN PATENT DOCUMENTS

| | | | |
|---|---|---|---|
| JP | 2010-246630 A | 11/2010 | |
| JP | 2011-067546 A | 4/2011 | |
| WO | WO-2006/065615 A1 | 6/2006 | |
| WO | WO-2008/132504 A1 | 11/2008 | |

OTHER PUBLICATIONS

Korean Office Action, w/ English translation thereof, issued in Korean Patent Application No. KR 10-2011-0126275 dated Dec. 20, 2012.

Extended European Search Report issued in European Patent Application No. EP 12169690.0 dated Jan. 4, 2013.

(Continued)

*Primary Examiner* — Sanjay Cattungal

(74) *Attorney, Agent, or Firm* — McDermott Will & Emery LLP

(57) ABSTRACT

A diagnosis apparatus and a method of operating the diagnosis apparatus. The diagnosis apparatus includes a probe for transmitting an ultrasonic wave signal to a subject and receiving a response signal; a data generating unit for generating image data of a plurality of frames, based on the response signal; a reliability determining unit for determining whether the image data is reliable by estimating a motion of the probe, based on the image data; a diagnosis unit for generating diagnosis data about the subject by using elastography, based on the image data; and a display device for displaying an image, based on the image data.

18 Claims, 12 Drawing Sheets

(56) References Cited

OTHER PUBLICATIONS

P. Foroughi et al., "Robust Elasticity Imaging Using External Tracker," Biomedical Imaging: From NANO to MACRO, 2009, ISBI '09, IEEE International Symposium on IEEE, XP031502012.
P. Foroughi et al., "Application of External Tracking in Ultrasound Elasticity Imaging," Proc. of SPIE 2010, vol. 7629, Feb. 13, 2010, XP040534526.
Korean Notice of Allowance, w/ English translation thereof, issued in Korean Patent Application No. KR 10-2011-0126275 dated May 16, 2013.
Lindop, Joel E. et al. "An Intelligent Interface for Freehand and Strain Imaging." Ultrasound in Medicine and Biology. vol. 34/ No. 7. pp. 1117-1128. Jul. 1, 2008.
Partial European Search Report issued in European Patent Application No. 12169690.0 dated Sep. 12, 2012.

* cited by examiner

DIAGNOSIS APPARATUS AND METHOD OF OPERATING THE SAME

CROSS-REFERENCE TO RELATED PATENT APPLICATION

This application claims the benefit of Korean Patent Application No. 10-2011-0126275, filed on Nov. 29, 2011, in the Korean Intellectual Property Office, the disclosure of which is incorporated herein in its entirety by reference.

BACKGROUND OF THE INVENTION

1. Field of the Invention

The present invention relates to a diagnosis apparatus and a method of operating the same.

2. Description of the Related Art

Elastography is a method of indicating the elasticity of a subject as an image. In elastography, the brightness and/or color of pixels of an image may be adjusted according to the elasticity of a subject. The elasticity of a subject may be obtained by strain of the subject due to a pressure applied to the subject.

The elasticity of a subject is related to a pathological phenomenon of the subject. Tumor tissues are harder than normal tissues. That is, since the elasticity of a tumor tissue is higher than the elasticity of a normal tissue, when the same pressure is applied to the tumor tissue and the normal tissue, the strain of the normal tissue is greater than the strain of the tumor tissue. Thus, elastography is used to diagnose tumor or cancer. For example, an elasticity contrast index (ECI) obtained by using elastography may be used to diagnose a nodule of a tissue. An ECI is obtained by quantifying a hardness difference between a nodule of a tissue and a normal tissue around the nodule. As an ECI increases, a nodule is harder, and the nodule is more likely to be malignant. In addition, elastography may be applied to various fields such as kidney transplant monitoring, skin and tissue engineering, cancer prognosis monitoring as well as detection and analysis of cancer or tumor.

Accordingly, there is a need for a diagnosis apparatus that effectively uses elastography and a method of operating the diagnosis apparatus.

SUMMARY OF THE INVENTION

The present invention provides a diagnosis apparatus that effectively uses elastography and a method of operating the same.

According to an aspect of the present invention, there is provided a diagnosis apparatus including a probe for transmitting an ultrasonic wave signal to a subject and receiving a response signal; a data generating unit for generating image data of a plurality of frames, based on the response signal; a reliability determining unit for determining whether the image data is reliable by estimating a motion of the probe, based on the image data; a diagnosis unit for generating diagnosis data about the subject by using elastography, based on the image data; and a display device for displaying an image, based on the image data.

The reliability determining unit may obtain a representative difference value of the plurality of frames, based on the image data and determines that the image data is reliable when the representative difference value is smaller than a reference value.

The reliability determining unit may group the plurality of frames into a plurality of sub durations, wherein the display device may display a plurality of reliability indicators, wherein the plurality of reliability indicators may have one-to-one correspondence to the plurality of sub durations, and wherein each of the plurality of reliability indicators may indicate reliabilities of a corresponding sub duration from among the plurality of sub durations.

The reliability determining unit may obtain a plurality of duration representative difference values that have one-to-one correspondence to the plurality of sub durations and obtains the representative difference value representing the plurality of duration representative difference values, and the display device may display the plurality of reliability indicators that indicate reliabilities, based on the duration representative difference values that correspond to the plurality of reliability indicators, respectively.

The display device may determine a selection color from among a plurality of colors for each respective reliability indicator, based on the duration representative difference values that respectively correspond to the plurality of reliability indicators, and displays each of the plurality of reliability indicators based on the selection color.

The plurality of colors may have one-to-one correspondence to a plurality of standard ranges, and the selection color may correspond to a standard range to which the duration representative difference value belongs, from among the plurality of standard ranges.

The display device may display the plurality of reliability indicators that indicate reliabilities of corresponding sub durations according to an order of the sub durations, in real time.

The reliability determining unit may obtain a plurality of initial difference values of the plurality of frames, based on the image data, and determines whether the image data is reliable based on the plurality of initial difference values.

The reliability determining unit may determine whether the image data is reliable based on at least one property of periodicity of the plurality of initial difference values and a variation degree of the plurality of initial difference values.

The diagnosis apparatus may further include a position estimating unit for generating position data by estimating a position of the probe with respect to the subject.

The position of the probe may include a roll rotation position of the probe and a yaw rotation position of the probe, and the position estimation unit may estimate the position of the probe, based on the image data.

The diagnosis apparatus may further include a storage unit for storing the image data, the diagnosis data, and the position data.

The display device may display a diagnosis screen in a diagnosis mode and displays a review screen in a review mode, wherein the diagnosis screen may include a subject image display portion for displaying an image of the subject, based on the image data; a strain map display portion for displaying a strain map, based on the image data; a reliability determination display portion for displaying a reliability marker indicating a reliability determination result of the reliability determining unit; a diagnosis result display portion for displaying a diagnosis result, based on the diagnosis data; and a position display portion for displaying a position indicator indicating a position of the probe, based on the position data.

The review screen may be displayed based on the image data, the diagnosis data, and the position data that is stored in the storage unit.

The display device may display a position indicator indicating the position of the probe, based on the position data.

According to another aspect of the present invention, there is provided a method of operating a diagnosis apparatus, the method including transmitting an ultrasonic wave signal to a subject and receiving a response signal, through a probe; generating image data of a plurality of frames, based on the response signal; determining whether the image data is reliable by estimating a motion of the probe, based on the image data; generating diagnosis data about the subject by using elastography, based on the image data; and displaying an image, based on the image data.

According to another aspect of the present invention, there is provided a computer-readable recording medium having recorded thereon a program for executing the method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. As used herein, the term "and/or" includes any and all combinations of one or more of the associated listed items.

Figure 1:
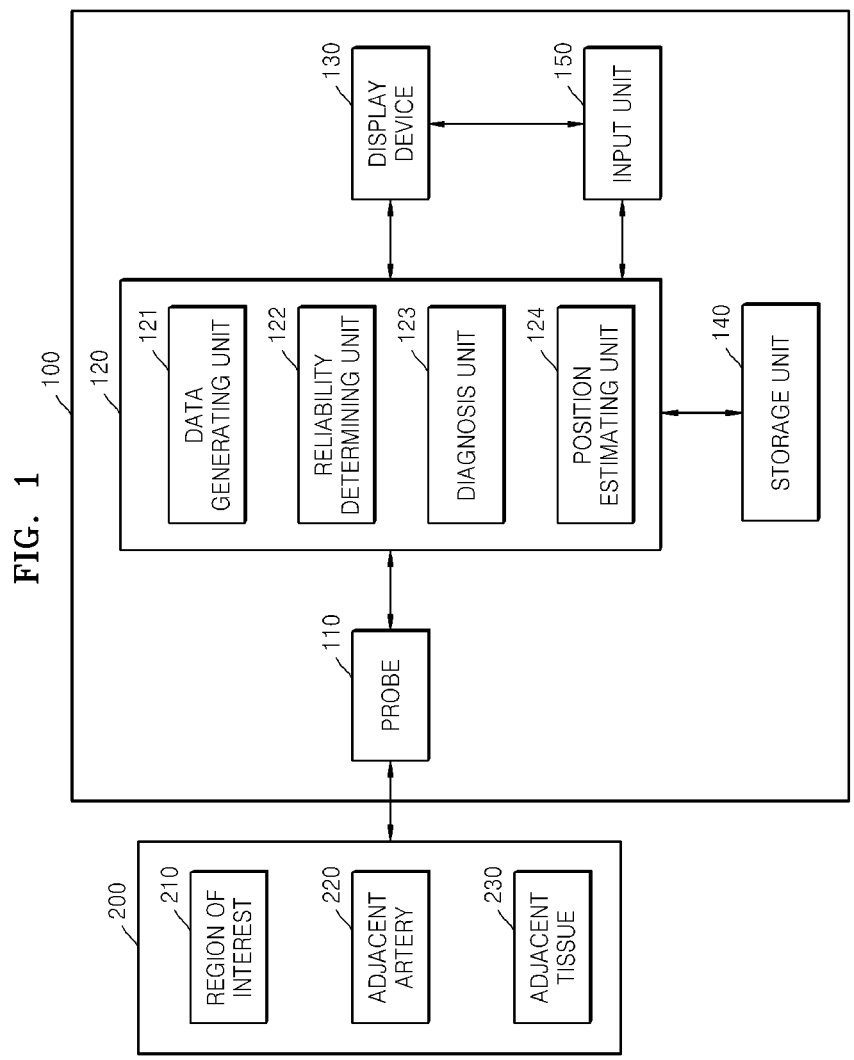
FIG. 1 is a block diagram of a diagnosis apparatus according to an embodiment of the present invention.

FIG. 1 is a block diagram of a diagnosis apparatus 100 according to an embodiment of the present invention.

Referring to FIG. 1, the diagnosis apparatus 100 may include a probe 110, a data processing unit 120, and a display device 130. The diagnosis apparatus 100 may further include a storage unit 140 and an input unit 150.

The probe 110 transmits an ultrasonic wave signal to a subject 200 and receives a response signal. The response signal may be a signal that is transmitted through the subject 200 or a signal that is reflected off the subject 200. The subject 200 may be an animal body such as a human body or a part of an animal body.

The subject 200 may include a region of interest 210 on which pathological diagnosis is performed by using elastography. The subject 200 may further include an adjacent artery 220 adjacent to the region of interest 210 and an adjacent tissue 230 adjacent to the region of interest 210. For example, when the region of interest 210 is the thyroid, the adjacent artery 220 may be the carotid artery and the adjacent tissue 230 may be the trachea.

The data processing unit 120 may generate data based on the response signal received by the probe 110 and may process the data. The data may include image data of a plurality of frames. The data processing unit 120 may process the image data of a plurality of frames so that an image may be displayed in real time. The data processing unit 120 may be embodied as a graphics processing unit (GPU) or the like.

The display device 130 may display an image based on the data processed by the data processing unit 120. The storage unit 140 may store the data. The input unit 150 may receive input information from user input. The input unit 150 may be displayed in the display device 130.

The data processing unit 120 may include a data generating unit 121, a reliability determining unit 122, and a diagnosis unit 123. The data processing unit 120 may further include a position estimating unit 124.

The data generating unit 121 may generate the image data of a plurality of frames, based on the response signal received by the probe 110. The image data may include elasticity data for displaying an elasticity image indicating the elasticity of the region of interest 210. The image data may include various kinds of data for displaying various kinds of images, in addition to the elastic data. For example, the image data may further include B mode data for displaying a B mode image, C mode data for displaying a C mode image, and contrast agent data for displaying a contrast agent image.

The elasticity of the region of interest 210 may frequently exert a stress on the region of interest 210 for a measurement duration and may be measured based on the image data of a plurality of frames that are obtained for the measurement duration. A pulse of the adjacent artery 220 may be used as the stress exerted on the region of interest 210. In addition, a user may exert a stress directly on the region of interest 210.

The reliability determining unit 122 estimates a motion of the probe 110 based on the image data of a plurality of frames and determines whether the image data is reliable. When the motion of the probe 110 falls within a permissible range for the measurement duration, a sectional view of the subject 200 with respect to the probe 110 may be maintained constant and the image data of a plurality of frames may be determined to be reliable. On the other hand, when the motion of the probe 110 does not fall within the permissible range for the measurement duration, the sectional view of the subject 200 with respect to the probe 110 may vary and the image data of a plurality of frames may not be determined to be reliable.

The diagnosis unit 123 generates diagnosis data about the subject 200 by using elastography based on the image data of a plurality of frames. The diagnosis unit 123 may generate the diagnosis data only when the image data is reliable. The diagnosis data may contain a benign or malignant degree of the region of interest 210. The benign or malignant degree of the region of interest 210 may be determined based on the elasticity data included in the image data and/or an elasticity contrast index (ECI).

Figure 2:
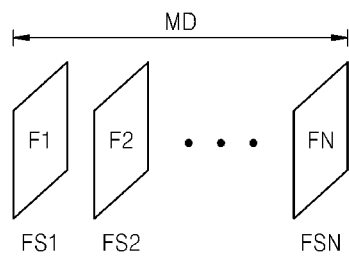
FIG. 2 is a diagram of image data of a plurality of frames, which is generated by a data generating unit of FIG. 1, according to an embodiment of the present invention.

FIG. 2 is a diagram of the image data of a plurality of frames, which is generated by the data generating unit 121 of FIG. 1, according to an embodiment of the present invention.

Referring to FIG. 2, the image data may contain a plurality of frame signals FS1, FS2, through FSN about a plurality of frames F1 through FN (where N is a natural number) that are obtained for a measurement duration MD. An $n^{th}$ frame signal FSn (n=1, 2, through N) may correspond to a matrix including a plurality of pixel values for an $n^{th}$ frame FN or may correspond to a representative value of the pixel values. The pixel values may correspond to data indicating the brightness and/or color of corresponding pixels, respectively. The pixel values may correspond to, but are not limited to, elasticity data for displaying an elasticity image. The representative value of the pixel values may be a single value that statistically represents the pixel values. For example, the representative value may be an average or standard deviation of the pixel values.

Figure 3:
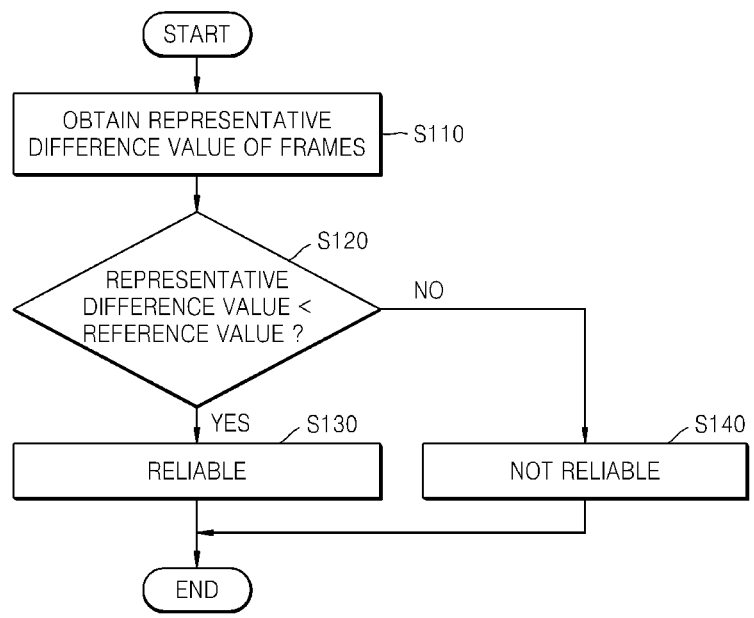
FIG. 3 is a flowchart of a method of a reliability determining unit of FIG. 1, for determining the reliability of image data of a plurality of frames, according to an embodiment of the present invention.

FIG. 3 is a flowchart of a method of the reliability determining unit 122 of FIG. 1, for determining the reliability of the image data of a plurality of frames, according to an embodiment of the present invention.

Referring to FIGS. 1 through 3, the reliability determining unit 122 obtains a representative difference value of the frames F1 through FN, based on the image data (S110). The reliability determining unit 122 may obtain the representative difference value based on the frame signals FS1, FS2, through FSN of the image data. The representative difference value is a value representing differences of the frame signals FS1, FS2, through FSN. The representative difference value may be obtained by using various statistical methods.

The reliability determining unit 122 determines whether the representative difference value is lower than a reference value (S120). The reference value may be set by a user. Alternatively, various reference values may be set according to the properties of the frame signals FS1, FS2, through FSN, the permissible range of the motion of the probe 110, the reliability of the image data, a period of stress, the properties of the subject 200, or the like.

If the representative difference value is lower than the reference value, the reliability determining unit 122 estimates that the motion of the probe 110 falls within the permissible range and determines that the image data is reliable (S130).

Otherwise, if the representative difference value is not lower than the reference value, the reliability determining unit 122 estimates that the motion of the probe 110 does not fall within the permissible range and determines that the image data is not reliable (S140).

The display device 130 illustrated in FIG. 1 may display a reliability marker indicating a result of reliability determination of the image data of the reliability determining unit 122. The user may recognize the result of the reliability determination through the reliability marker. The reliability marker may be displayed by using various methods, such as characters, colors, flicker, and the like.

Figure 4:
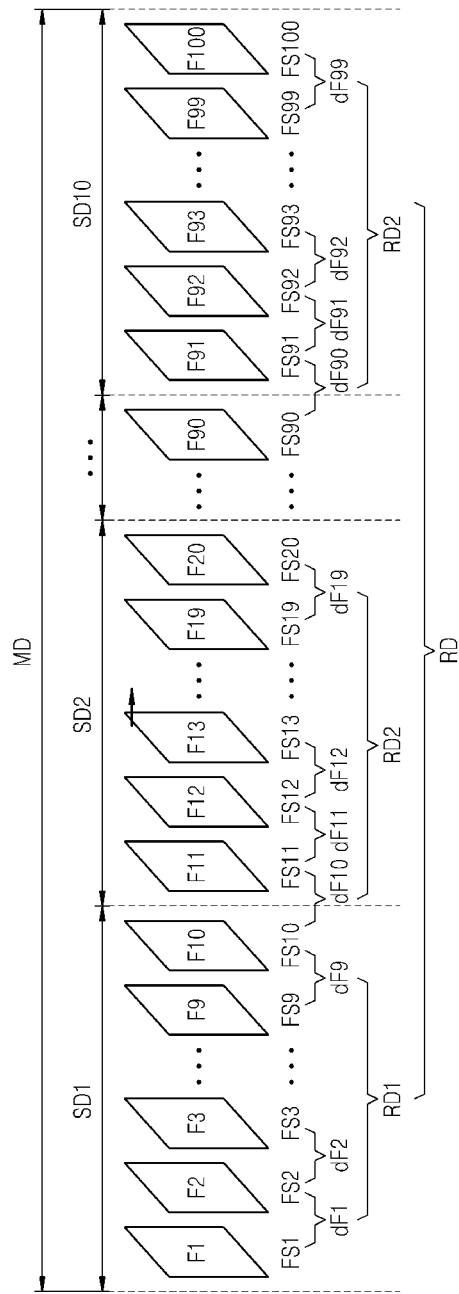
FIG. 4 is a diagram showing a method of obtaining a representative difference value of a plurality of frames in order to determine reliability, according to an embodiment of the present invention.

FIG. 4 is a diagram showing a method of obtaining a representative difference value RD of a plurality of frames F1 through F100 in order to determine reliability, according to an embodiment of the present invention.

Referring to FIGS. 1 and 4, the data generating unit 121 may generate a plurality of frame signals FS1 through FS100 about the frames F1 through F100 during measurement duration MD. The reliability determining unit 122 may divide the measurement duration MD into a plurality of sub durations SD1 through SD10 and may group the frames F1 through F100 into the sub durations SD1 through SD10. For example, the second sub duration SD2 may include the $11^{th}$ frame F11 to the $20^{th}$ frame F20.

For convenience of description, FIG. 4 shows a case where 100 frame signals FS1 through FS100 are obtained during the measurement duration MD and the measurement duration MD includes 10 sub durations SD1 through SD10. However, the case shown in FIG. 4 is just an example, and the number of frames and sub durations are not limited to any particular number.

The reliability determining unit 122 may obtain a plurality of difference values dF1 through dF99 based on the frame signals FS1 through FS100. Each of the difference values dF1 through dF99 may be obtained based on two adjacent frame signals. For example, the second difference value dF2 may be obtained by subtracting the second frame signal FS2 from the third frame signal FS3. When the frame signals FS1 through FS100 correspond to a matrix, the second difference value dF2 may be a representative value of elements included in a difference matrix obtained by matrix-subtracting the second frame signal FS2 from the third frame signal FS3.

A plurality of duration representative difference values RD1 through RD10 may be obtained for the respective sub durations SD1 through SD10. For example, the $2^{nd}$ duration representative difference value RD2 that statistically represents the $10^{th}$ difference value dF10 through the $19^{th}$ difference value dF19 may be obtained in the second sub duration SD2.

A representative difference value RD may be a value that statistically represents the duration representative difference values RD1 through RD10.

Figure 5:
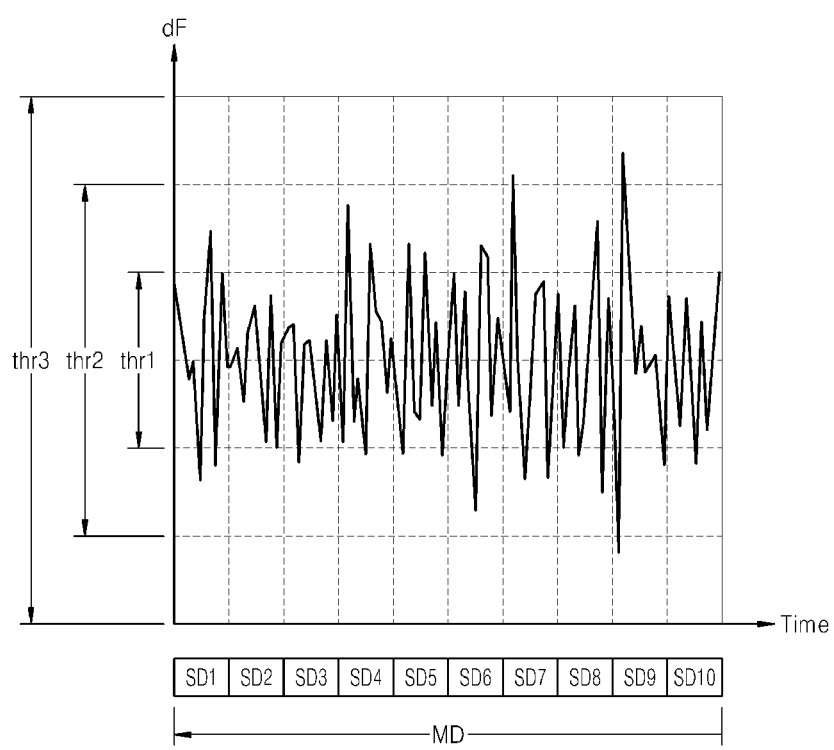
FIG. 5 is a difference graph showing a plurality of difference values of a plurality of frames, according to an embodiment of the present invention.

FIG. 5 is a difference graph showing a plurality of difference values of a plurality of frames, according to an embodiment of the present invention.

Referring to FIG. 5, a horizontal axis indicates time and a vertical axis indicates a difference value dF. The difference value dF may fall within one reference range of a plurality of reference ranges thr1, thr2, and thr3. It may be estimated that, as an absolute value of the difference value dF increases, a motion of the probe 110 (refer to FIG. 1) is increased.

The display device 130 (refer to FIG. 1) may display the difference graph of FIG. 5 in real time. A user may intuitively recognize the motion of the probe 110 (refer to FIG. 1) from the difference graph and thus may adjust the motion of the probe 110 (refer to FIG. 1) in real time.

In addition, the display device 130 (refer to FIG. 1) may display a plurality of reliability indicators that have one-to-one correspondence to the sub durations SD1 through SD10. The reliability indicators may indicate the reliability of sub durations that respectively correspond thereto. From the reliability indicators, the user may intuitively recognize the motion of the probe 110 (refer to FIG. 1).

Figure 6:
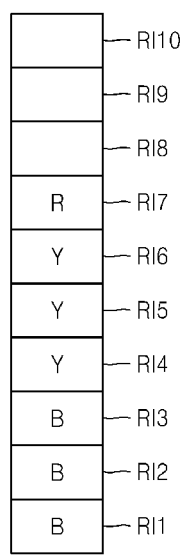
FIG. 6 is a diagram showing a plurality of reliability indicators displayed on a display device of FIG. 1, according to an embodiment of the present invention.

FIG. 6 is a diagram showing a plurality of reliability indicators RI1 through RI10 displayed on the display device 130 of FIG. 1, according to an embodiment of the present invention.

Referring to FIGS. 4 through 6, the reliability indicators RI1 through RI10 have one-to-one correspondence to the sub durations SD1 through SD10. The reliability indicators RI1 through RI10 may indicate the reliability of sub durations that respectively correspond thereto based on duration representative difference values of the sub durations, respectively. For example, the second reliability indicator RI2 may indicate the reliability of the second sub duration SD2 based on a second duration representative difference value RD2 that is a duration representative difference value of the second sub duration SD2.

The reliability indicators RI1 through RI10 may indicate the reliabilities of sub durations that correspond thereto by using selection colors from among a plurality of colors, respectively. For example, the reliability indicators RI1 through RI10 may emit selection colors, respectively. A reliability indicator of which a selection color is not determined from among the reliability indicators RI1 through RI10 may not emit light.

A selection color from among a plurality of colors may be determined based on a duration representative difference value of a corresponding sub duration. Difference colors may be respectively assigned to the reference ranges thr1, thr2, and thr3. In addition, a selection color may be determined according to a reference range to which a duration representative difference value belongs. For example, a first reference range thr1 may correspond to blue, a second reference range thr2 may correspond to yellow, and a third reference range thr3 may correspond to red.

In FIG. 6, it is assumed that all duration representative difference values of first through third sub durations SD1 through SD3 fall within the first reference range thr1, all duration representative difference values of fourth through sixth sub durations SD4 through SD6 fall within a second reference range thr2, and a duration representative difference value of the seventh sub duration SD7 falls within the third reference range thr3. In addition, it is assumed that the eighth duration SD8 proceeds and a duration representative difference value of the eighth duration SD8 is not obtained. Thus, first through third reliability indicators RI1 through RI3 may emit blue B, fourth through sixth reliability indicators RI1 through RI3 may emit yellow Y, and the seventh reliability indicator RI7 may emit red R. In addition, eighth through tenth reliability indicators RI8 through RI10 may not emit light.

The reliability indicators RI1 through RI10 may indicate the reliabilities of the sub durations SD1 through SD10 in real time according to an order of the sub durations SD1 through SD10. For example, the first reliability indicator RI1 may indicate the reliability of the first sub duration SD1, and the next remaining reliability indicators RI2 through RI20 may sequentially indicate the reliabilities of corresponding sub durations.

In addition, prior to respectively obtaining duration representative difference values for the sub durations SD1 through SD10, the reliability indicators RI1 through RI10 may indicate the reliability of a corresponding sub duration based on the difference value dF obtained in real time in the corresponding sub duration. For example, after the first reliability indicator RI1 indicates the reliability of the first sub duration SD1, before a second duration representative difference value RD2 of the second sub duration SD2 is obtained, the second reliability indicator RI2 may indicate the reliabilities of sub durations according to an order in which tenth through ninth difference values dF10 through dF19 are obtained. In detail, the second reliability indicator RI2 determines a selection color based on the 10th difference value dF10 and may emit the selection color. Then, the second reliability indicator RI2 may determine selection colors according to an order in which the remaining difference values dF11 through dF19 are obtained and may emit the selection colors. When the second duration representative difference value RD2 representing the tenth through ninth difference values dF10 through dF19 is obtained, the second reliability indicator RI2 may determine a selection color based on the second duration representative difference value RD2 and may emit the selection color.

A user may intuitively and easily recognize the motion of the probe 110 (refer to FIG. 1) from the reliability indicators RI1 through RI10 and thus may adjust the motion of the probe 110 (refer to FIG. 1) in real time.

Figure 7:
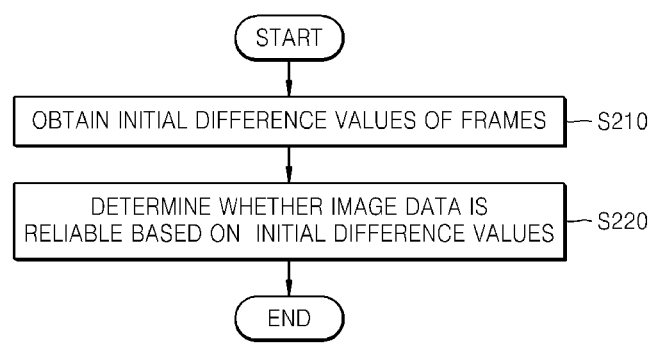
FIG. 7 is a flowchart of a method of a reliability determining unit of FIG. 1 for determining the reliability of image data of a plurality of frames, according to another embodiment of the present invention.

FIG. 7 is a flowchart of a method of the reliability determining unit 122 of FIG. 1 for determining the reliability of image data of a plurality of frames, according to another embodiment of the present invention.

Referring to FIGS. 1, 2 and 7, the reliability determining unit 122 may obtain a plurality of initial difference values of a plurality of frames F1 through FN, based on image data generated by the data generating unit 121 (S210). An $n^{th}$ initial difference value of an $n^{th}$ frame may be a difference between an $n^{th}$ frame signal FSn and a first frame signal FS1. When the $n^{th}$ frame signal FSn corresponds to a matrix, the $n^{th}$ initial difference value may be a representative value of elements included in a difference matrix obtained by matrix-subtracting the first frame signal FS1 from the $n^{th}$ frame signal FSn.

The reliability determining unit 122 may determine whether the image data is reliable based on a plurality of initial difference values (S220). The reliability determining unit 122 may determine whether the image data is reliable based on at least one property from among the periodicity and variation degree of a plurality of initial difference values.

When a motion of the probe 110 falls within a permissible range, the initial differences may have periodicity. Thus, whether the motion of the probe 110 falls within the permissible range may be estimated according to the periodicity of the initial difference values.

When the motion of the probe 110 falls within the permissible range, the variation degree of the initial difference values may be smaller than a reference value. Thus, whether the motion of the probe 110 falls within the permissible range may be estimated according to the variation degree of the initial difference values. The reference value may be set by a user or may be variously set according to the properties of a plurality of frame signals FS1, FS2, through FSN, the permissible range of the motion of the probe 110, the reliability of image data, a period of stress, the properties of the subject 200, or the like.

Figure 8:
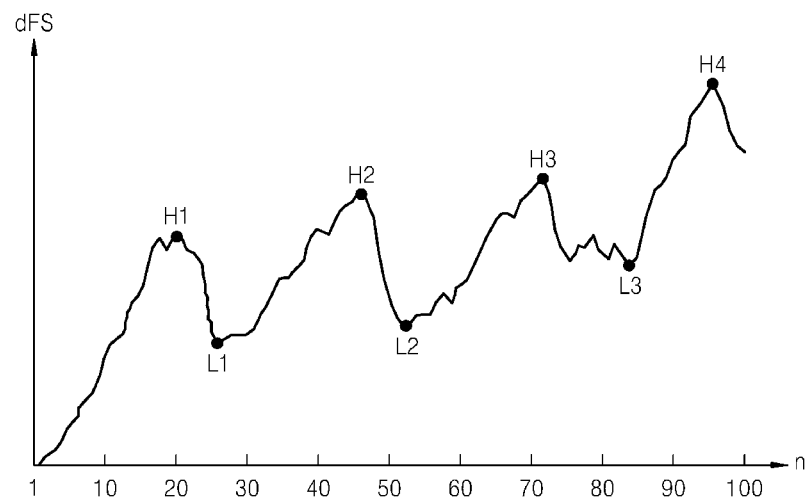
FIGS. 8 and 9 are initial difference graphs showing initial differences indicating a plurality of initial difference values of a plurality of frames, according to an embodiment of the present invention.
Figure 9:
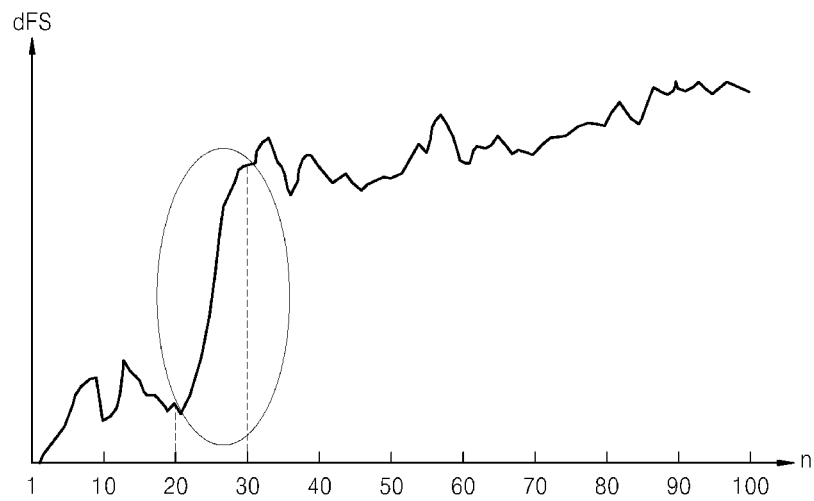

FIGS. 8 and 9 are initial difference graphs showing initial differences indicating a plurality of initial difference values dFS of a plurality of frames, according to an embodiment of the present invention.

Referring to FIGS. 1, 8, and 9, a horizontal axis indicates a frame number n and a vertical axis indicates an initial difference value dFS. According to the frame number n, the initial difference values dFS may have a pattern in which an increase and a reduction are repeatedly exhibited. The initial difference values dFS may include a plurality of peaks H1 through H4 and a plurality of inverse peaks L1 through L3.

The reliability determining unit 122 may determine whether the image data is reliable based on at least one property from among the periodicity and variation degree of the initial difference values dFS.

A method of determining whether the image data is reliable based on the periodicity of the initial difference values dFS will now be described.

For example, the periodicity of the initial difference values dFS may be determined based on the peaks H1 through H4 and the inverse peaks L1 through L3. When an interval between the first peak H1 and the second peak H2 deviates from a reference period range, the reliability determining unit 122 may estimate that the motion of the probe 110 deviates from the permissible range and may determine that the image data is not reliable. The reference period range may be determined based on a period of stress that is applied to the subject 200.

When all intervals between neighboring peaks H1 and H2, H2 and H3, and H3 and H4 fall within the reference period range, the reliability determining unit 122 may estimate that the motion of the probe 110 falls within the permissible range and may determine that the image data is reliable.

Similarly, a degree of motion of the probe 110 may be estimated based on the inverse peaks L1 through L3.

When an interval between the first peak H1 and the first inverse peak L1 deviates from a reference half-period range, the reliability determining unit 122 may estimate that the motion of the probe 110 deviates from the permissible range and may determine that the image data is not reliable.

A method of determining whether the image data is reliable based on the deviation degree of the initial difference values dFS will now be described.

The deviation degree of the initial difference values dFS may be determined by a difference between neighboring initial difference values with a reference value. For example, a difference between an $n^{th}$ initial difference value dFSn and a $(n+m)^{th}$ initial difference value dFSn+m (m is a natural number) may be compared with the reference value. The reference value and m may be variously set in consideration of the permissible range of the motion of the probe 110. In FIG. 9, it may be determined that a difference between a $20^{th}$ initial difference value dFS20 and a $30^{th}$ initial difference value dFS30 may be greater than the reference value. Thus, the reliability determining unit 122 may estimate that the motion of the probe 110 deviates from the permissible range and may determine that the image data is not reliable.

Referring back to FIG. 1, the position estimating unit 124 may estimate a position of the probe 110 with respect to the subject 200 and may generate position data.

The position estimating unit 124 may estimate the position of the probe 110 with respect to the subject 200 through a position sensor (not shown). The position estimating unit 124 may estimate the position of the probe 110 based on the image data generated by the data generating unit 121.

The position of the probe 110 may include a roll rotation position of the probe 110 and a yaw rotation position of the probe 110.

Figure 10:
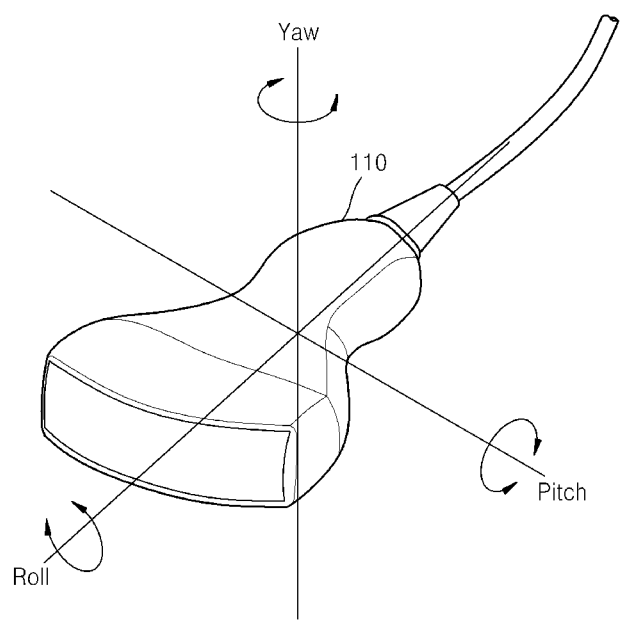
FIG. 10 is a diagram showing roll rotation, pitch rotation, and yaw rotation of a probe of FIG. 1, according to an embodiment of the present invention.
Figure 11:
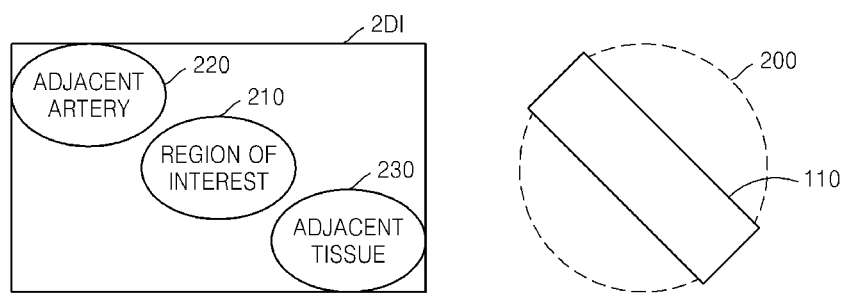
FIGS. 11 through 14 show examples of a case whether a position of the probe of FIG. 1 is estimated, according to embodiments of the present invention.
Figure 12:
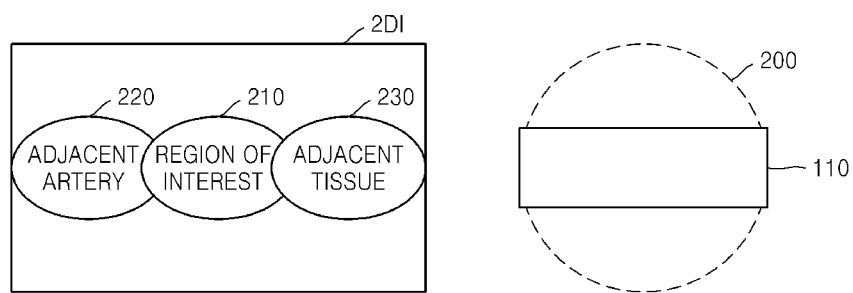
Figure 13:
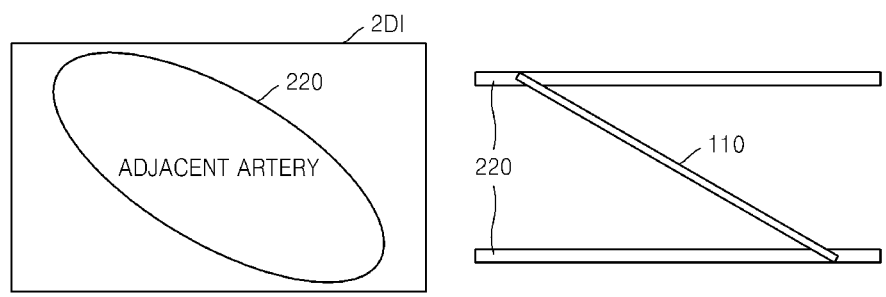
Figure 14:
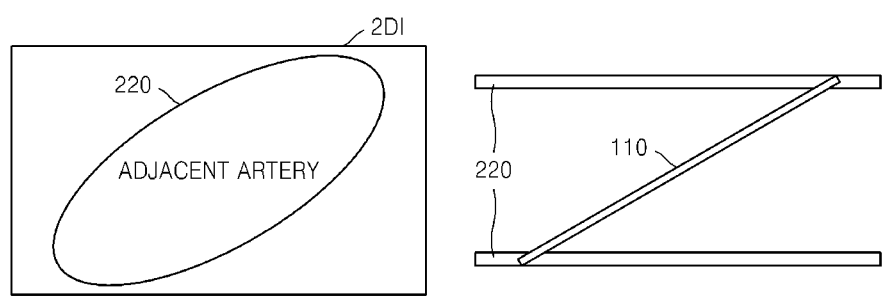

FIG. 10 is a diagram showing roll rotation, pitch rotation, and yaw rotation of the probe 110 of FIG. 1, according to an embodiment of the present invention. FIGS. 11 through 14 show examples of a case whether a position of the probe 110 of FIG. 1 is estimated, according to embodiments of the present invention.

Referring to FIGS. 1 and 10 through 12, the position estimating unit 124 may estimate a sectional view of the probe 110 with respect to the subject 200 by estimating inclination that is formed by the region of interest 210, the adjacent artery 220, and the adjacent tissue 230 on a two-dimensional image (2DI). The position estimating unit 124 may estimate the roll rotation of the probe 110 by estimating the sectional view of the probe 110 with respect to the subject 200. The image data generated by the data generating unit 121 may include 2D data for displaying the 2DI.

The position estimating unit 124 may identify positions of the region of interest 210, the adjacent artery 220, and the adjacent tissue 230 based on a brightness difference of pixels and may estimate the inclination on the 2DI. On the 2DI, the positions of the region of interest 210, the adjacent artery 220, and the adjacent tissue 230 may be input by a user through the input unit 150.

Referring to FIGS. 1, 10, 13, and 14, the position estimating unit 124 may estimate the sectional view of the probe 220 with respect to the adjacent artery 220 by estimating the shape of the adjacent artery 220 on the 2DI. The position estimating unit 124 may estimate the yaw rotation position of the probe 110 by estimating the sectional view of the probe 110 with respect to the adjacent artery 220.

The storage unit 140 may store the position data generated by the position estimating unit 124. The display device 130 may display a position indicator for indicating the position of the probe 110 based on the position data.

Figure 15:
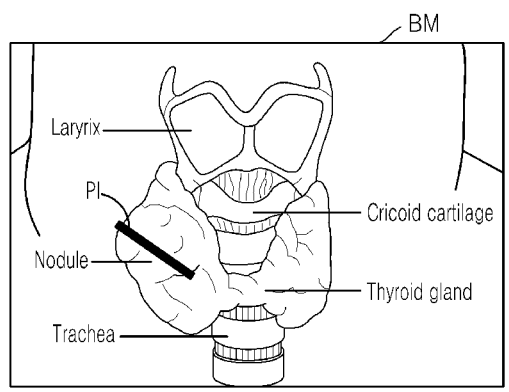
FIG. 15 is a diagram of a position indicator displayed on the display device of FIG. 1, according to an embodiment of the present invention.

FIG. 15 is a diagram of a position indicator displayed on the display device 130 of FIG. 1, according to an embodiment of the present invention.

Referring to FIGS. 1 and 15, the display device 130 may display a position indicator PI on a body marker BM about the subject 200.

Like in FIG. 15, when the body marker BM is a two-dimensional image, the position indicator PI displayed on the body marker BM may indicate only the roll rotation position of the probe 110. The position indicator PI may further include a yaw rotation indicator for indicating only a yaw rotation position of the probe 110. For example, the yaw position indicator may have the shape of the adjacent artery 220 on the 2DI (refer to FIGS. 13 and 14).

Unlike in FIG. 15, when the body marker BM is a three-dimensional image, the position indicator PI may be indicated as a two-dimensional image so as to indicate the roll rotation position and yaw rotation position of the probe 110.

When the storage unit 140 stores position data and the display device 130 displays a position indicator based on the position data, a tracking test may be easily performed. This is because the same sectional view of the subject 200 needs to be rediagnose after a time passes, in order to perform a tracking test. The diagnosis apparatus 100 may rediagnose the same sectional view as a sectional view of the subject 200, which is previously diagnosed, based on the position data and the position indicator.

The diagnosis apparatus 100 may operate in a diagnosis mode or a review mode. The diagnosis apparatus 100 in the diagnosis mode may obtain data of the subject 200 through the probe 110 and may diagnose the subject 200. The diagnosis apparatus 100 in the review mode may review the subject 200 based on the data stored in the storage unit 140.

Figure 16:
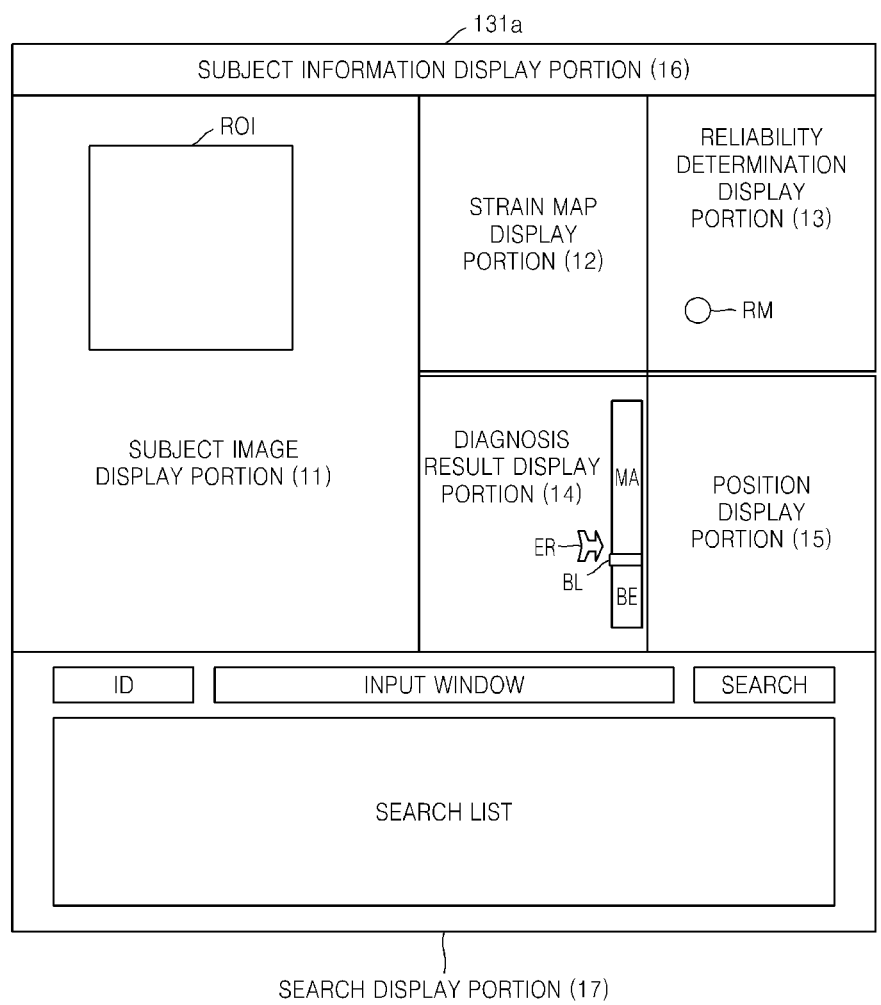
FIG. 16 is a diagram of a diagnosis screen displayed on the display device of FIG. 1 that operates in a diagnosis mode, according to an embodiment of the present invention.

FIG. 16 is a diagram of a diagnosis screen 131a displayed on the display device 130 of FIG. 1 that operates in a diagnosis mode, according to an embodiment of the present invention. FIG. 16 shows an example of the diagnosis screen 131a. The present invention is not limited to the arrangement of parts of the diagnosis screen 131a of FIG. 16.

Referring to FIGS. 1 and 16, the diagnosis screen 131a of the display device 130 may include a subject image display portion 11, a strain map display portion 12, a reliability determination display portion 13, a diagnosis result display portion 14, and a position display portion 15.

An image of the subject 200 may be displayed on the subject image display portion 11, based on the image data generated by the data generating unit 121. A B mode image, a C mode image, or a contrast agent image may be displayed on the subject image display portion 11. Alternatively, the B mode image, the C mode image, and the contrast agent image may be blended and displayed on the subject image display portion 11 or may be separately displayed. When a contrast agent is used, image quality may be lowered due to a low mechanical index (MI). Thus, the B mode image, the C mode image, and the contrast agent image may be registered and displayed on the subject image display portion 11.

A region of interest (ROI) box may be displayed on the subject image display portion 11. The ROI box may be automatically displayed on the region of interest 210, or alternatively, the ROI box may be input by a user through the input unit 150 and may be displayed.

A strain map may be displayed on the strain map display portion 12, based on the image data. The strain map may be an image formed by combining a plurality of elasticity images of a plurality of frames. The strain map may be obtained by combining a plurality of elasticity images of a plurality of frames by using a statistical method, such as an average, an intermediate value, counting the number of pixels, whose pixel value exceeds a reference value. The strain map may be generated by processing a portion in the ROI box of the subject image display portion 11. The diagnosis apparatus 100 may reduce overhead of generation of the strain map by using the ROI box.

A reliability marker RM for indicating a reliability determination result of the reliability determining unit 122 may be displayed on the reliability determination display portion 13. When the reliability determining unit 122 determines that the image data is reliable, the reliability marker RM may be activated. The activity of the reliability marker RM may be displayed by using a method where the reliability marker RM emits light.

The reliability determination display portion 13 may further display a process of estimation of the motion of the probe 110 as well as the reliability marker RM in order to determine reliability by the reliability determining unit 122. As shown in FIG. 6, the reliability indicators RI1 through RI10 may be displayed on the reliability determination display portion 13. As shown in FIGS. 5, 8, and 9, a difference graph, an initial difference graph, and the like may be displayed on the reliability determination display portion 13. A user may recognize in real time whether the sectional view of the subject 200 with respect to the probe 110 is maintained, through the reliability determination display portion 13.

When the reliability marker RM is not activated, the image data generated by the data generating unit 121 is not reliable. Thus, when the reliability marker RM is not activated, the diagnosis unit 123 may not diagnose the subject 200. When the reliability marker RM is not activated, the diagnosis apparatus 100 may obtain data of the subject 200 again through the probe 110.

When the reliability marker RM is activated, the image data is reliable. Thus, when the reliability marker RM is activated, the diagnosis unit 123 may diagnose the subject 200 based on the image data.

When the reliability marker RM is activated, the diagnosis unit 123 may automatically diagnose the subject 200 based on the image data. Otherwise, when the reliability marker RM is activated, the user may order the diagnosis unit 123 to diagnose the subject 200 based on the image data, through the input unit 150.

A diagnosis result ER of the diagnosis unit 123 may be displayed on the diagnosis result display portion 14. The diagnosis result ER may indicate whether the region of interest 210 of the subject 200 is benign BE or malignant MA. In addition, the diagnosis result ER may indicate a benign BE or malignant MA degree of the region of interest 210. The benign BE or malignant MA degree may be displayed by a distance between the diagnosis result ER and a boundary BL of benign BE or malignant MA. The boundary BL of benign BE or malignant MA may be set from an experiment result of clinical evaluation. FIG. 16 is only an example of the diagnosis result ER. In addition, the diagnosis result ER may be displayed by using various methods.

Position indicators based on the position data generated by the position estimating unit 124 may be displayed on the position display portion 15. For example, as shown in FIG. 15, the position indicators may be displayed on the position display portion 15.

As such, in a case of a diagnosis mode, a subject image and a strain map may be simultaneously viewed from diagnosis screen 131a of the display device 130. Since the motion of the probe 110 is estimated through the reliability determination display portion 13, the user may recognize whether the sectional view of the subject 200 with respect to the probe 110 is maintained.

The diagnosis screen 131a may further include a subject information display portion 16 and a search display portion 17. Subject information for identifying the subject 200, such as identification (ID) for identifying the subject 200, a diagnosis date, or the like may be displayed on the subject information display portion 16.

The search display portion 17 may display a search list and an interface for inputting ID to an input window and performing a search. When an icon indicated in the search list is clicked after a search is performed, the diagnosis screen 131a of the display device 130 may be converted into a review mode.

Figure 17:
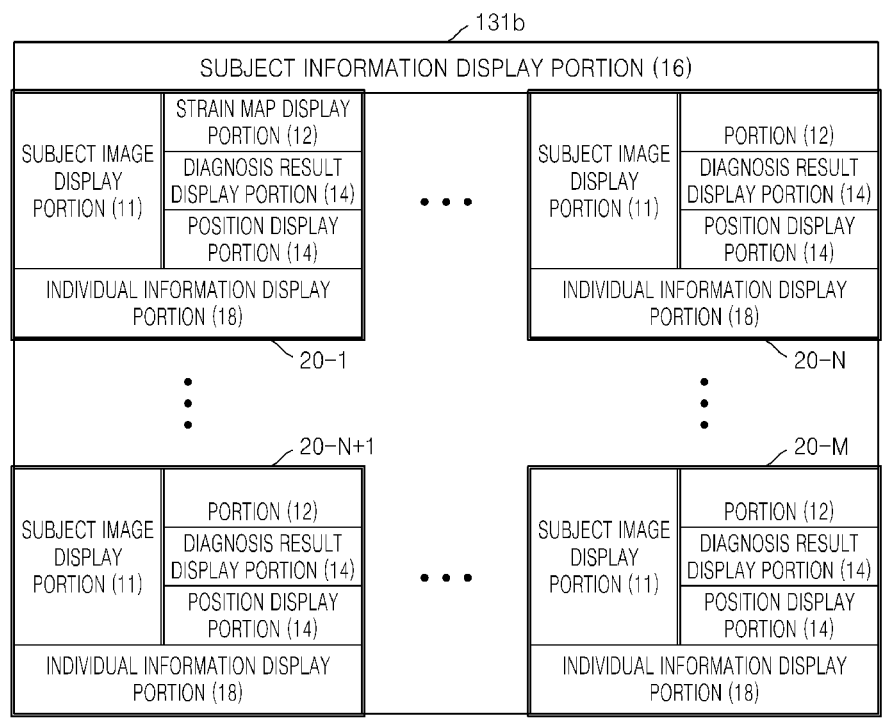
FIG. 17 is a diagram of a review screen displayed on the display device of the diagnosis apparatus that operates in a review mode, according to an embodiment of the present invention.

FIG. 17 is a diagram of a review screen 131b displayed on the display device 130 of the diagnosis apparatus 100 that operates in a review mode, according to an embodiment of the present invention. FIG. 17 shows an example of the review screen 131b. The present invention is not limited to the arrangement of parts of the review screen 131b of FIG. 17.

Referring to FIGS. 1 and 17, the review screen 131b may include parts displayed on the diagnosis screen 131a (refer to FIG. 16). Like reference numerals of the diagnosis screen 131a of FIG. 16 denote like elements, and thus, their description is omitted.

The review screen 131b may include the subject information display portion 16 and at least one diagnosis information display portion 20-1 through 20-M. The at least one diagnosis information display portion 20-1 through 20-M may display information obtained by diagnosing the same subject as the subject 200 on different dates. In the review screen 131b, the at least one diagnosis information display unit 20-1 through 20-M may be aligned in a time sequence. Thus, a tracking test may be performed from the review screen 131b.

The review screen 131b may be displayed on the display device 130, based on data stored in the storage unit 140.

Each of the diagnosis information display portions 20-1 through 20-M may include a subject image display portion 11, a strain map display portion 12, a diagnosis result display portion 14, and a position display portion 15. Each of the diagnosis information display units 20-1 through 20-M may not include the reliability determination display portion 13, unlike the diagnosis screen 131a of FIG. 16. This is because only image data that is determined to be reliable in a diagnosis mode is a subject to be reviewed.

Each of the diagnosis information display portions 20-1 through 20-M may further include individual information display portion 18. A diagnosis date or the like may be displayed on the individual information display portion 18.

As such, according to one or more embodiments of the present invention, a diagnosis apparatus may effectively use elastography.

A diagnosis apparatus according to one or more embodiments of the present invention may obtain reliable image data of a plurality of frames by estimating a motion of a probe.

The diagnosis apparatus may display a process of estimating the motion of the probe in real time. Thus, a user may easily and intuitively estimate the motion of the user and may recognize in real time whether a sectional view of a subject with respect to the probe is maintained. Thus, the user may appropriately adjust the motion of the probe in real time.

The diagnosis apparatus may store position data that is generated by estimating a position of the probe with respect to the subject. Thus, the diagnosis apparatus may review the same sectional view as a sectional view of the subject, which is previously diagnosed. Accordingly, a tracking test may be easily performed.

According to one or more embodiments of the present invention, a diagnosis apparatus and a method of operating the diagnosis apparatus may effectively use elastography.

The embodiments of the present invention can be written as computer programs and can be implemented in general-use digital computers that execute the programs using a computer-readable recording medium. Data structure used in the above-described method may be recorded in a computer-readable recording medium by using various methods. Examples of the computer-readable recording medium include magnetic storage media (e.g., ROM, RAM, USB, floppy disks, hard disks, etc.) and storage media such as optical recording media (e.g., CD-ROMs, or DVDs) and PC interfaces (e.g., PCI, PCI-express, Wifi, etc.).

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A diagnosis apparatus comprising:
a probe for transmitting an ultrasonic wave signal to a subject and receiving a response signal;
a data generating unit for generating image data of a plurality of frames, based on the response signal;
a reliability determining unit for grouping the plurality of frames into a plurality of sub durations, and determining whether the image data is reliable by estimating a motion of the probe based on difference values between frames included in the plurality of frames;
a diagnosis unit for generating diagnosis data about the subject by using elastography, based on the image data; and
a display device for displaying an image based on the image data and displaying a plurality of reliability indicators based on a reliability determination result of the reliability determining unit,
wherein the plurality of reliability indicators have one-to-one correspondence to the plurality of sub durations, and each of the plurality of reliability indicators indicates reliabilities of a corresponding sub duration from among the plurality of sub durations.

2. The diagnosis apparatus of claim 1, wherein the reliability determining unit obtains a plurality of difference values between adjacent frames included in the plurality of frames, obtains a plurality of duration representative difference values which represent difference values in each of the plurality of sub durations, obtains a representative difference value which represents the plurality of duration representative difference values, and determines that the image data is reliable when the representative difference value is smaller than a reference value.

3. The diagnosis apparatus of claim 2,
wherein the display device displays the plurality of reliability indicators that indicate reliabilities, based on the duration representative difference values that correspond to the plurality of reliability indicators, respectively.

4. The diagnosis apparatus of claim 3, wherein the display device determines a selection color from among a plurality of colors for each respective reliability indicator, based on the duration representative difference values that respectively correspond to the plurality of reliability indicators, and displays each of the plurality of reliability indicators based on the selection color.

5. The diagnosis apparatus of claim 4, wherein the plurality of colors have one-to-one correspondence to a plurality of standard ranges, and
wherein the selection color corresponds to a standard range to which the duration representative difference value belongs, from among the plurality of standard ranges.

6. The diagnosis apparatus of claim 2, wherein the display device displays the plurality of reliability indicators that indicate reliabilities of corresponding sub durations according to an order of the sub durations, in real time.

7. The diagnosis apparatus of claim 1, wherein the reliability determining unit obtains a plurality of initial difference values of the plurality of frames, based on the image data, and determines whether the image data is reliable based on the plurality of initial difference values.

8. The diagnosis apparatus of claim 6, wherein the reliability determining unit determines whether the image data is reliable based on at least one property of periodicity of the plurality of initial difference values and a variation degree of the plurality of initial difference values.

9. The diagnosis apparatus of claim 1, further comprising a position estimating unit for generating position data by estimating a position of the probe with respect to the subject.

10. The diagnosis apparatus of claim 9, wherein the position of the probe comprises a roll rotation position of the probe and a yaw rotation position of the probe, and
wherein the position estimation unit estimates the position of the probe, based on the image data.

11. The diagnosis apparatus of claim 9, further comprising a storage unit for storing the image data, the diagnosis data, and the position data.

12. The diagnosis apparatus of claim 11, wherein the display device displays a diagnosis screen in a diagnosis mode and displays a review screen in a review mode,
wherein the diagnosis screen comprises:
a subject image display portion for displaying an image of the subject, based on the image data;
a strain map display portion for displaying a strain map, based on the image data;
a reliability determination display portion for displaying a reliability marker indicating a reliability determination result of the reliability determining unit;
a diagnosis result display portion for displaying a diagnosis result, based on the diagnosis data; and
a position display portion for displaying a position indicator indicating a position of the probe, based on the position data.

13. The diagnosis apparatus of claim 12, wherein the review screen is displayed based on the image data, the diagnosis data, and the position data that are stored in the storage unit.

14. The diagnosis apparatus of claim 13, wherein the display device displays a position indicator indicating the position of the probe, based on the position data.

15. A method of operating a diagnosis apparatus, the method comprising:
    transmitting an ultrasonic wave signal to a subject and receiving a response signal, through a probe;
    generating image data of a plurality of frames, based on the response signal;
    grouping the plurality of frames into a plurality of sub durations;
    determining whether the image data is reliable by estimating a motion of the probe based on difference values between frames included in the plurality of frames;
    generating diagnosis data about the subject by using elastography, based on the image data; and
    displaying an image based on the image data and displaying a plurality of reliability indicators based on a reliability determination result of a reliability determining unit,
    wherein the plurality of reliability indicators have one-to-one correspondence to the plurality of sub durations, and each of the plurality of reliability indicators indicates reliabilities of a corresponding sub duration from among the plurality of sub durations.

16. The method of claim 15, wherein the determining comprises:
    obtaining a plurality of difference values between adjacent frames included in the plurality of frames;
    obtaining a plurality of duration representative difference values which represent difference values in each of the plurality of sub durations;
    obtaining a representative difference value which represents the plurality of duration representative difference values; and
    determining that the image data is reliable when the representative difference value is smaller than a reference value.

17. The method of claim 16,
    wherein the displaying comprises displaying the plurality of reliability indicators that indicate reliabilities, based on the duration representative difference values that correspond to the plurality of reliability indicators, respectively.

18. A non-transitory computer-readable recording medium having recorded thereon a program for executing the method of claim 15.

* * * * *